US006190696B1

(12) United States Patent
Groenewoud

(10) Patent No.: US 6,190,696 B1
(45) Date of Patent: Feb. 20, 2001

(54) STABILIZED THYROXINE MEDICATIONS

(76) Inventor: Pieter J. Groenewoud, 4 Westover Ct., Yardley, PA (US) 19067

( * ) Notice: Under 35 U.S.C. 154(b), the term of this patent shall be extended for 0 days.

(21) Appl. No.: 09/327,256

(22) Filed: Jun. 7, 1999

Related U.S. Application Data

(63) Continuation-in-part of application No. 09/092,819, filed on Jun. 8, 1998, now abandoned.

(51) Int. Cl.$^7$ .............................. A61K 9/20; A61K 38/00
(52) U.S. Cl. .................... 424/464; 424/465; 424/475; 514/5
(58) Field of Search ..................... 424/464, 465, 424/475; 514/5

(56) References Cited

U.S. PATENT DOCUMENTS 5,225,204 * 7/1993 Chen et al. ..................... 424/484
5,635,209 * 6/1997 Groenewoud et al. ............... 424/464

OTHER PUBLICATIONS

Rapaka et al. facile hydrolytic cleavage of N,O–diheptafluorobutyryl devitaives of thyroidal amino acids. J. Chromatography. vol. 236:496–498, 1982.*

Nakamura et al. Formation and Reduction of ascorbate radicals by hog thyroid microsomes, Archives of Biochemistry and Biophysics. vol. 305: 84–90, Aug. 1, 1993.*

* cited by examiner

Primary Examiner—Thurman K. Page
Assistant Examiner—Lakshmi Channavajjala
(74) Attorney, Agent, or Firm—Zachary T. Wobensmith, III

(57) ABSTRACT

Thyroxine medications which include combinations of levothyroxine, and/or liothronine, or dextrothyroxine, or thyroid, and one or more iodine salts, or iodine donor compounds are described, which produce a stable thyroxine medication, with a long shelf life. A method for manufacturing the medications is also described.

8 Claims, No Drawings

STABILIZED THYROXINE MEDICATIONS

CROSS REFERENCE TO RELATED APPLICATIONS

This application is a continuation in part of my prior application Ser. No. 09/092,819 Filed Jun. 8, 1998, now abandoned.

Thyroxine and Liothyronine containing medications are and have been used for many years to treat thyroid deficiency and related illnesses. In administering thyroxine and or liothyronine products it is important to assure that the patient is receiving the correct dose, customized to his or her particular needs.

Many individual tablet strengths are available to allow the physician to titrate their patients accurately.

An example is Levothyroxine Sodium that is available in 10 individual strengths ranging from 25–300 mcg per tablet.

This group of compounds can be extracted from glands or made synthetically. A well known problem encountered by many manufacturers of these products is their inherent thermo-labile nature. These compounds degrade rapidly during their shelf life causing sub-potency that can potentially lead to under-medicated patients.

In order to compensate for this rapid degradation, manufacturers customarily add an excess of the active ingredient.

This in turn has led to super potent product being released to the market that lose a significant percentage of their potency over their claimed shelf life.

Most if not all products currently available have potency inconsistencies over their shelf life.

The use of super potent products is of course as undesirable as the use of sub potent products.

Although these products have been offered for many years without FDA approval (thyroxine products are "grand fathered"), the FDA has stated that it requires manufacturers to file a New Drug Application with the agency.

As reason FDA stated in a Federal Register notice in August 1997 that "no currently marketed orally administered levothyroxine sodium product has been shown to demonstrate consistent potency and stability and, thus, no currently marketed levothyroxine is generally recognized as safe and effective" FDA noted that "almost every manufacturer of orally administered levothyroxine sodium products, including the market leader, has reported recalls that were the result of potency or stability problems."

Since 1991, the agency reported, "there have been no less than 10 firm-initiated recalls of levothyroxine sodium tablets involving 150 lots and more than 100 mil. tablets. In all but one case, the recalls were initiated because tablets were found to be subpotent or potency could not be assured through the expiration date."

Stability problems with levothyroxine products have been the subject of two warning letters since 1991. FDA said "this pattern of stability problems suggests that the customary two-year shelf life may not be appropriate for these products because they are prone to experience accelerated degradation in response to a variety of factors."

To further increase the quality of care provided to patients with insufficient thyroid function it is important to provide access to medication that has a consistent potency over its claimed shelf life. This will allow the endocrinologist to accurately titrate their patients without the potential that variation in thyroxine batches will cause clinical changes and considerable discomfort to the patient that can even result in hospitalization.

DESCRIPTION OF THE PRIOR ART

Various prior art formulations are disclosed in the U.S. Patents to Kummer, et al., U.S. Pat. No. 4,110,470; Miller, et al., U.S. Pat. No. 4,585,652; Anderson, et al., U.S. Pat. No. 4,818,531; Sloan, U.S. Pat. No. 5,001,115; Ginger, et al., U.S. Pat. No. 2,889,363;Ginger, et al., U.S. Pat. No. 2,889, 364; Chen, et al. U.S. Pat. No. 5,225,204; and Groenewoud, et al., U.S. Pat. No. 5,635,209.

In the U.S. Pat. No. 2,889,364; Chen et al., methods are described using poloxamer and other compounds as a stabilizing complex former in combination with levothyroxine and cellulose compounds. It also describes the use of cellulose compounds alone as the stabilizer in both dry and solvent based processes. A major disadvantage of a wet granulation process in particular when water and heat is used as stated in this patent is that one will have to compensate in advance for the degradation that will occur during the process leaving unknown degradation products in the finished stabilized product. The use of cellulose compound to achieve stabilization in dry processes will circumvent this, however the stabilizing effect of cellulose compounds is limited and much less effective than for example Sodium Iodide.

Chen, et al. also teach to avoid the use of lactose and other saccharides since these compounds are known to degrade thyroxine medications more rapidly. Some of these well accepted excipients have very desirable tableting characteristics and can be used in my invention after careful isolation of thyroxine in granules composed of a stabilizing matrix and the active compound. Yet another disadvantage is the use of some of the solvents that are suggested such as methylene dichloride and methanol that are quite toxic and for which the United States Pharmacopoeia XXIII (USP), has extremely low acceptance limits for residues of these substances in the finished product. Current chemical processes mostly avoid chlorinated and other toxic solvents altogether wherever possible. In my new invention only purified water or ethanol is used before contact with thyroxine to avoid initial degradation. In my new invention heat is only used in a process step before the thyroxine or liothyronine is added for the same reason not to cause any initial degradation. Water of course is non-toxic and ethanol has very limited toxicity, if any, at the level used in my invention. Chen et al. also suggests the use of calcium phosphate, calcium carbonate and calcium sulfate. However in a letter (Letters—Mar. 11, 1998) to the Journal of the American Medical Association, researchers report reduction of levothyroxine efficacy if used simultaneously with calcium carbonate. The report furthers states "Calcium carbonate itself or, alternatively excipients or contaminants in the preparation could form insoluble chelates with levothyroxine."

In my new invention the use of calcium and other multivalent ions is avoided to further improve the stability and efficacy of the medication.

In my prior U.S. Pat. No. 5,635,209 a method is described wherein levothyroxine sodium titration is physically combined with potassium iodide and other ingredients to form a more stable formulation.

While the composition described in U.S. Pat. No. 5,635, 209 is suitable for its intended use it has several limitations and disadvantages. For example potassium iodide is used in varying levels ranging from 0.1% to 0.7%. Although the levels suggested for the lower strengths do not exceed recommended daily allowances (RDA) the higher levels do exceed this level. This can potentially lead to undesirable effects caused by excess iodine intake especially when these medications are taken in combination with multivitamin and mineral combinations. For example Flintstones® multi vitamin tablets for children and other brands contain 150 mcg of iodine which is equivalent to the RDA.

A carefully selected level of iodine compounds in my new invention is less than the daily recommended allowance.

In my new invention only one level is used for the lower as well as the higher strengths and in one particular process described in my new invention far less than the normal daily intake. Yet the stabilizing effect is sufficient to provide significantly improved stability without any concern about the high iodide levels, especially for the pediatric patient population.

Another disadvantage of the use of potassium iodide is the potential of metathesis with Levothyroxine sodium. The potassium from the potassium iodide can potentially take the place of the sodium on the thyroxine molecule and vice versa. This can potentially lead to a change in the dissolution rate and essentially change the compound from the identity claimed on the label of the medication. My new invention describes the use of sodium iodide which does not present this undesirable potential reaction.

Also U.S. Pat. No. 5,635,209 does not include the combination products of levothyroxine sodium and liothryronine sodium or thyroid gland preparation furthermore it only describes the process of stabilizing levothyroxine sodium in the finished product.

My new invention describes a way to stabilize the raw materials itself to increase the flexibility in which the invention can be used as described in the examples of the invention. In addition to the increased flexibility of the use of this stabilized levothyroxine or liothyronine concentrate it brings the level of the suitable iodine salts down to levels that are far less than the RDA and therefore do not add significantly to normal dietary and/or supplemental intake.

Also neither one of the two inventions describe the use of antioxidants. This new invention will show how an antioxidant can be effectively used to further aid in the stabilization if the said medications.

Levothyroxine Sodium and Liothyronine Sodium Stability

The instability of levothyroxine and liothyronine has been known for a long time. Levothyroxine and liothyronine are degrade through oxidation and or de-iodination and other excipient/active interactions in which de-iodination appears to be the predominant degradation pathway.

Of interest is the article by Rapaka et al. that describes the difference between the stability of liothyronine and levothyroxine. The two co-valently bound iodine atoms in the 1 and 5 position are the least stable, once 1 iodine atom becomes detached the resulting compound is even less stable and more likely to lose the second iodine atom.

The inventions demonstrates that levothyroxine and liothyronine can be stabilized by embedding the active particles in a matrix that contains an effective stabilizer in the form of an iodide salt of for example sodium. The resulting action is stabilization of the levothyroxine particle without it being necessary that the stabilizing agents interact by surrounding the individual thyroxine molecules.

One would expect to see better stabilizing action the more iodide is used however an optimum concentration is reached around 0.1% iodide and above approximately 0.3% iodide in a 100 mg tablet containing 100 mcg levothyroxine sodium it starts to interfere with the stability of the active compound.

Since another degradation pathway is oxidation the addition of a specially prepared antioxidant will further aid in the stabilization of levothyroxine sodium and liothyronine sodium.

Further degradation can be prevented through careful selection of excipients that have proper tableting or encapsulation characteristics without exerting destabilizing effects on the active compounds.

Such compounds are for example but not limited to:

Microcrystalline cellulose, especially newly introduced grades by FMC: Avicel® (brand name of microcrystalline cellulose) PH-112, and low moisture grade specifically developed for moisture sensitive products with a mean particle size of 90 micron this grade is free flowing to facilitate tableting with good weight control. Avicel PH-113, also low moisture but with a smaller particle size to better facilitate wet granulations with for example alcohol. Avicel® PH-200 is a large particle grade specifically used as a tableting binder with superior flow characteristics. Avicel® PH-301, PH302 and the older products PH-101, PH-102 can also be used in a satisfactory manner although the older grades may have some minor disadvantages as it relates to product flow and moisture content. The most recent innovation in the microcrystalline cellulose product line is Ceolus®, also introduced by FMC. Ceolus® can be used to produce hard tablets because of its flatter structure than regular microcrystalline cellulose; it is prepared from wood pulp from specially selected grades of wood.

Mendel offers a similar product line for microcrystalline cellulose, as Emcocel® and generic equivalents for the older types are also available. Grades of microcrystalline are typically used as dry binders in tableting, in wet granulations since they can absorb significant quantities of liquids because of their porous structure, as diluents in powders for encapsulation and as carriers for actives and or excipients.

Grades of microcrystalline cellulose also exert some disintegration properties and are considered chemically inert towards most active ingredients.

A newly introduced innovation by Mendel is Prosolv™ or silicified microcrystalline cellulose, which is a highly compressible co-processed combination of microcrystalline cellulose with colloidal silicon dioxide.

It has superior tableting characteristics and is offered in two grades, one for wet granulations (Prosolv SMCC™50) and one as a dry binder/diluent (Prosolv SMCC™90). Although it has different characteristics compared to regular microcrystalline cellulose it has retained all desired properties of these compounds.

As disintegrant several compounds can be used such as sodium starch glycolate especially Explotab® CLV, that through high cross linking has a lower viscosity than the regular grade and has a more robust disintegration action compared to regular sodium starch glycolate.

Another suitable disintegrant is Emcosoy® offered by Mendel as a kosher product. Encosoy® consists of soy polysaccharides and a non-ionic effective disintegrant. Alginic acid is another disintegrant that may be used. Mendel offers alginic acid under the trade name Satialgine™ H8.

As lubricant magnesium stearate or other stearates may be used however the preferred lubricant is Sodium Stearyl Fumarate since it does not have the potential to chelate the levothyroxine sodium by donating multi valent alkali or other metal ions.

Mendel offers Stearyl Fumarate sodium under the trade name Pruv™. Another useful lubricant is hydrogenated vegetable oil, offered by Mendel under the name Lubritab®. Lubritab® is chemically less reactive than other commonly used lubricants and therefore has excellent formulation compatibility.

EXAMPLE 1

The following example covers the stabilization of two different strengths of levothyroxine and compares the stabilizing effect with a control formulation, using only microcrystalline cellulose and other excipients as well as a commercially available preparation. The formulations were compared after being subjected to accelerated stability conditions of 60° Celsius for 14 days.

The products were analyzed on a daily basis to measure the amount of potency loss in percent of the label claim.

In order to prepare the control formulation and the stabilized formulation a levothyroxine trituration was prepared as follows.

Composition of the Levothyroxine Tituration

| | |
|---|---:|
| Levothyroxine Sodium Microfine (hydrous) | 27.14 g |
| Microcrystalline Cellulose | 100.0 g |
| Microcrystalline Cellulose | 100.0 g |
| Microcrystalline Cellulose | 200.0 g |
| Microcrystalline Cellulose | 400.0 g |
| Microcrystalline Cellulose | 1572.86 g |
| Total: | 2400.0 g |

The microcrystalline cellulose is de-agglomerized through a 40 mesh screen before use. Mix the levothyroxine sodium with 100 gram of the microcrystalline cellulose and mix intensively (this can be achieved in a large mortar and pestle). Pass the so obtained mixture through a 60 mesh screen to finely disperse the active though the microcrystalline cellulose (carrier). Add another 100 gram of microcrystalline cellulose and mix again. Repeat the screening step through the 60 mesh screen. This mixture is further triturated with the remaining microcrystalline cellulose being added in to similar steps. After the 200 and 400 g microcrystalline cellulose are added this mixture is now charged into a V-blender equipped with an intensifier bar together with 1572.86 g of microcrystalline cellulose.

The blender is started with the intensifier bar activated and blended for three minutes.

The resulting blend, off-white with acceptable flow characteristics, has basically a similar appearance as regular microcrystalline cellulose.

Preparation of Stabilizer/Carrier Mixture

| | |
|---|---:|
| microcrystalline cellulose | 28.46 kg |
| sodium iodide | 40 g |
| Total: | 28.50 kg |

Procedure

The sodium iodide is dissolved in 5700 mL of purified water in a suitable stainless steel container at room temperature. The stabilizer rapidly dissolves and the resulting solution is clear and colorless.

The microcrystalline cellulose is charged into a planetary blender of suitable size, in this case a Hobart mixer was used but other pharmaceutical granulation equipment may be used alternatively.

Before adding the stabilizer solution the moisture content of the microcrystalline cellulose is measured. This moisture level will be used as the target moisture content after drying.

The mixer is started and the solution is now slowly added to the microcrystalline cellulose until all has been dispersed and a homogeneous mixture is obtained. The material so obtained is a damp granular mixture and is transferred to drying racks for drying in a drying oven at 60° Celsius until a moisture content of ±1% of the initial value is obtained. Alternatively drying of this mixture can be done in standard pharmaceutical dryers such as fluid bed dryers manufactured by Glatt or Aeromatic. Drying temperature can also be varied but extremely high temperatures should be avoided.

After drying the material was screened through a 30 mesh screen and collected in suitable containers until further processed. The resulting powder is off-white with acceptable flow characteristics and similar in appearance as regular microcrystalline cellulose. The process is repeated until sufficient material is obtained for further processing of the finished product batches.

Manufacturing of Stabilized and Control Tablets

Stabilized levothyroxine tablets of 25 mcg and 100 mcg were made as follows.

| 25 mcg tablets stabilized | | |
|---|---:|---:|
| | Per Tablet | Per Batch |
| levothyroxine tituration | 2.50 mg | 32.50 g |
| microcrystalline cellulose | 10.85 mg | 141.05 g |
| stabilizer/carrier mixture | 95.00 mg | 1235 g |
| crosscarmellose sodium | 1.10 mg | 14.30 g |
| magnesium stearate | 0.55 mg | 7.15 g |
| Total: | 110.0 mg | 1430.00 g |

Charge the following ingredients into a small V-blender: levothyroxine tituration, microcrystalline cellulose, stabilizer/carrier mixture, crosscarmellose sodium after screening through a 40 mesh screen and blend for 15 minutes. Add after passing though a 40 mesh screen magnesium stearate and continue to blend for 3 more minutes.

The mixture is used to compress tablets with an average tablet target weight of 110 mg. A Colton tablet press was used equipped with compression tools of 9/32' in diameter. The tablets obtained had a hardness of 4–6 kp with a thickness of 3.4–3.6 mm. The tablets disintegrated very rapidly.

| 100 mcg tablets stabilized | | |
|---|---:|---:|
| | Per Tablet | Per Batch |
| levothyroxine tituration | 10.00 mg | 130.00 g |
| microcrystalline cellulose | 3.35 mg | 43.55 g |
| stabilizer/carrier mixture | 95.00 mg | 1235 g |
| crosscarmellose sodium | 1.10 mg | 14.30 g |
| magnesium stearate | 0.55 mg | 7.15 g |
| Total: | 110.0 mg | 1430.0 g |

Charge the following ingredients into a small V-blender: levothyroxine tituration, microcrystalline cellulose, stabilizer/carrier mixture, crosscarmellose sodium after screening through a 40 mesh screen and blend for 15 minutes. Add after passing though a 40 mesh screen magnesium stearate and continue to blend for 3 more minutes.

The mixture is used to compress tablets with an average tablet target weight of 110 mg. A Colton tablet press was used equipped with compression tools of 9/32' in diameter.

The tablets obtained had a hardness of 4–6 kp with a thickness of 3.4–3.6 mm. The tablets disintegrated very rapidly.

Both batches were packaged in HDPE containers of a size and shape typical of those used in the pharmaceutical industry, and stored in a stability chamber at a temperature of 60° Celsius to evaluate the effectiveness of the stabilizer.

| 25 mcg tablets control | | |
|---|---|---|
| | Per Tablet | Per Batch |
| levothyroxine tituration | 2.50 mg | 50.00 g |
| microcrystalline cellulose | 105.85 mg | 2117.00 g |
| crosscarmellose sodium | 1.10 mg | 22.00 g |
| magnesium stearate | 0.55 mg | 11.00 g |
| Total: | 110.0 mg | 2200.0 g |

Charge the following ingredients into a small V-blender: levothyroxine tituration, microcrystalline cellulose, crosscarmellose sodium after screening through a 40 mesh screen and blend for 15 minutes. Add after passing though a 40 mesh screen magnesium stearate and continue to blend for 3 more minutes.

The mixture is used to compress tablets with an average tablet target weight of 110 mg. A Colton tablet press was used equipped with compression tools of 9/32' in diameter. The tablets obtained had a hardness of 4–6 kp with a thickness of 3.4–3.6 mm. The tablets disintegrated very rapidly.

| 100 mcg tablets stabilized | | |
|---|---|---|
| | Per Tablet | Per Batch |
| levothyroxine tituration | 10.00 mg | 200.00 g |
| microcrystalline cellulose | 98.35 mg | 1967.00 g |
| crosscarmellose sodium | 1.10 mg | 22.00 g |
| magnesium stearate | 0.55 mg | 11.00 g |
| Total: | 110.0 mg | 2200.00 g |

Charge the following ingredients into a small V-blender: levothyroxine tituration, microcrystalline cellulose, stabilizer/carrier mixture, crosscarmellose sodium after screening through a 40 mesh screen and blend for 15 minutes. Add after passing though a 40 mesh screen magnesium stearate and continue to blend for 3 more minutes.

The mixture is used to compress tablets with an average tablet target weight of 110 mg. A Colton tablet press was used equipped with compression tools of 9/32' in diameter. The tablets obtained had a hardness of 4–6 kp with a thickness of 3.4–3.6 mm. The tablets disintegrated very rapidly.

Both batches were packaged in HDPE containers of a size and shape typical of those used in the pharmaceutical industry, and stored in a stability chamber at a temperature of 60° Celsius to provide a control formulation to compare against the stabilized version using a sodium iodide. All four batches were tested to evaluate content uniformity per USP and all four passed with a wide margin confirming sufficient mixing of the blend.

The tablets that were subjected to stress conditions were tested on a daily basis to measure potency loss using a current USP liquid chromatographic procedure. The results displayed in the following tables and figures clearly demonstrate the effectiveness of sodium iodide.

Results for the 100 mcg batches showed similar degradation patterns and again demonstrated the superior action of the sodium iodide versus the control batch and the commercial product.

To suppress analytical variability the results were evaluated using linear regression and through interpolation a more accurate set of results was obtained than the unprocessed data. The following table displays the results of the regression analysis.

| Levothyroxine batches after 14 days stress conditions [60° C.] | | | | | | | |
|---|---|---|---|---|---|---|---|
| | day 2 | day 4 | day 6 | day 8 | day 10 | day 12 | day 14 |
| Lot Description [25 mcg]: | | | | | | | |
| Commercial Product | 3.7% | 7.2% | 10.7% | 14.1% | 17.7% | 21.2% | 24.7% |
| Control batch + desiccant in container | 6.2% | 8.5% | 10.7% | 13.0% | 15.2% | 17.5% | 19.7% |
| Stabilized batch + desiccant in container | 0.3% | 1.3% | 2.3% | 3.3% | 4.3% | 5.3% | 6.3% |
| Control batch No desiccant in container | 5.1% | 8.3% | 11.5% | 14.8% | 18.0% | 21.2% | 24.4% |
| Stabilized batch No desiccant in container | 0.4% | 1.7% | 3.0% | 4.2% | 5.5% | 6.7% | 8.0% |
| Lot Description [100 mcg]: | | | | | | | |
| Commercial Product | 7.5% | 10.0% | 12.6% | 15.1% | 17.6% | 20.1% | 22.6% |
| Control batch + desiccant in container | 7.0% | 8.9% | 10.9% | 12.8% | 14.7% | 16.6% | 18.6% |
| Stabilized batch + desiccant in container | 2.6% | 3.2% | 3.8% | 4.4% | 5.0% | 5.6% | 6.2% |
| Control batch No desiccant in | 5.9% | 8.0% | 10.1% | 12.2% | 14.3% | 16.4% | 18.5% |

-continued

Levothyroxine batches after 14 days stress conditions [60° C.]

| | day 2 | day 4 | day 6 | day 8 | day 10 | day 12 | day 14 |
|---|---|---|---|---|---|---|---|
| container | | | | | | | |
| Stabilized batch No desiccant in container | 3.5% | 4.4% | 5.4% | 6.3% | 7.3% | 8.2% | 9.1% |

To further evaluate the effectiveness of the invention three scale-up batches were prepared of 200,000 tablets each. This time a 300 mcg tablet was included. A 300 mcg is typically the highest strength that is commercially offered.

The batches were prepared in a similar fashion as the smaller scale batches however same design equipment, but much larger was used. The batches processed the same way and testing showed that all USP specifications could be met with a wide margin. The tablets were tested to include assay, content uniformity and dissolution.

To eliminate the analytical variability sometimes encountered the results would processed using linear regression techniques. The results acquired through interpolation confirm earlier findings as follows.

Storage at 60° C. tested after the listed number of days (Levothyroxine Tablets)

| Lot Description [Scale-up study]: | 2 | 4 | 6 | 8 | 10 | 12 | 14 | 30 |
|---|---|---|---|---|---|---|---|---|
| 25 mcg batch size 200,000 | 2.9% | 3.4% | 3.9% | 4.4% | 4.9% | 5.5% | 6.0% | 10.1% |
| 100 mcg batch size 200,000 | 2.7% | 3.0% | 3.3% | 3.6% | 3.8% | 4.1% | 4.4% | 8.7% |
| 300 mcg batch size 200,000 | 2.5% | 2.9% | 3.3% | 3.7% | 4.1% | 4.5% | 4.9% | 8.1% |

From the experiment it is clear that scale-up does not have an adverse effect on the stabilization effectiveness of sodium iodide to prevent accelerated loss of potency seen in the control batches and commercially available products.

Further studies confirmed that the stabilized products using sodium iodide are not considered thermo-labile under USP guidelines. The commercially available product and the control batches are considered thermo-labile using these guidelines and would require labeling as such.

EXAMPLE 2

This example describes a method to decrease the amount of stabilizer used in the final formulation significantly, by making an intermediate product consisting of granules containing levothyroxine sodium co-processed with stabilizer/carrier.

| Ingredient | Amount per batch |
|---|---|
| Levothyroxine sodium microfine (hydrous) | 9.05 g |
| Carrier/stabilizer (from example 1) | 200.00 g |
| Carrier/stabilizer (from example 1) | 200.00 g |
| Carrier/stabilizer (from example 1) | 390.95 g |
| Total: | 800.00 g |

Preparation of Granules

All ingredients are de-agglomerized by using a 40 mesh screen for the stabilizer/carrier and a 60 mesh screen for the active ingredient. The levothyroxine sodium microfine (hydrous) is intimately mixed with 200 g of Carrier/stabilizer (from example 1) in a high shear granulator such as a Robocoupe® or equivalent for approximately 5 minutes. The mixture so obtained is transferred to a V-blender with intensifier bar and 200 g of Carrier/stabilizer (from example 1) is added. The mixture is blended with the intensifier bar engaged for 10 minutes. To this mixture 390.95 g of Carrier/stabilizer (from example 1) is added and mixing is continued for 10 more minutes. The resulting blend is compressed into tablets using ¼" compression tooling. The tablets are now milled using an oscillating granulator fitted with a 0.5 mm screen. The granular material obtained is screened using a 40 mesh and a 100 mesh screen. The fraction that is smaller than 40 mesh but larger than 100 mesh is collected. The fractions that are not acceptable are recycled by compression into tablets and subsequent milling and repetition of the screening to obtain the desired granular fraction. A yield of approximately 80% can be expected.

Is granular free-flowing material consists of stabilized levothyroxine granulation and can be further processed into tablets or capsules if so desired.

Tablets can be manufactured according to the following procedure.

Levothyroxine 300 mcg tablets [batch size 10,000 tablets]

| Ingredients: | Per tablet | Per batch |
|---|---|---|
| Stabilized levothyroxine granulation (40–100 mesh) | 30.00 mg | 300.00 g |
| Prosolv ™ SMCC 50 (Silicified microcrystalline sodium) granulation 40–100 mesh | 65.00 mg | 650.00 g |
| Emcosoy ® (soy polysaccharides) | 4.00 mg | 40.00 g |
| Sodium Stearyl Fumarate | 1.00 mg | 10.00 g |
| Total: | 100.00 mg | 1000.00 g |

Procedure

An excess of Prosolv™ SMCC 50 is compressed into tablets. The tablets are now milled using an oscillating granulator fitted with sharp edge 0.5 mm screen. The granular material obtained is screened using a 40 mesh and a 100 mesh screen. The fraction that is smaller than 40 mesh but larger than 100 mesh is collected. The fractions that are not acceptable are recycled by compression into tablets and subsequent milling and repetition of the screening to obtain the desired granular fraction. From this mixture 650.00 g is weighed for further processing.

Add to a small V-blender Prosolv™ SMCC 50 (Silicified microcrystalline sodium) granulation 40–100 mesh, stabilized levothyroxine granulation (40–100 mesh) and Emcosoy® (soy polysaccharides). The mixture is blended for 15 minutes. Add the sodium stearyl fumarate and blend for an additional 3 minutes.

The resulting blend is compressed into tablets using 9/32" diameter compression tooling with an average target weight of 100 mg. Elegant tablets can be obtained because of the superior compression characteristics of Prosolv™. The levothyroxine granules are unlikely to fracture during compression since microcrystalline cellulose undergoes plastic deformation during compression. Therefore the particle integrity of the stable levothyroxine granules is retained. In this invention Prosolv™ or other porous materials can be used as a carrier for suitable iodide compounds, but it is important to quickly process the carrier/stabilizer mixture further into its final dosage form. Finely divided iodine on a carrier as powder, is exposed to air and can potentially form iodates which in turn interfere with the stabilizing properties of iodine compounds.

The tablets so obtained are stable and contain only a fraction of the RDA of iodine and therefore do not add significantly to the dietary intake and/or supplemental intake of iodine. The 300 mcg tablets obtained using this process only contain 25% of the RDA of iodine. Tablets of the lower strengths utilizing this process will contain even smaller amounts. For example the 25 mcg and 100 mcg tablets customarily used for the pediatric population, contain no more than approximately 2% and 8% respectively, of the RDA for iodine. The potential for excessive iodine intake is practically eliminated. This process can of course also be used for levothyroxine sodium and liothyronine sodium combinations or for liothyronine alone. The liothyronine will have to be added to the levothyroxine and carrier/stabilizer mixture and than further processed as described earlier. The stabilized granules can also be further processed by coating of the particles, familiar to those skilled in the art, by using methacrylic resins. The granules now have a superior protection from other excipients and can be combined with ingredients that are considered incompatible with thyroxine or liothyronine such as lactose or other reducing carbohydrates. Reducing carbohydrates can interact with the secondary amine group that is present on these compounds. However proper isolation of the granules will prevent such interaction.

EXAMPLE 3
Stabilizer/carrier Mixture (SMCC/stabilizer)

| | |
|---|---|
| Prosolv ® SMCC 50 (silicified microcrystalline cellulose) | 29.55 kg |
| Sodium iodide | 45.00 g |
| Ethyl alcohol | 500.00 mL |
| Total (after drying): | 30.00 kg |

Dissolve the sodium iodide it the alcohol in a stainless steel container at room temperature. The resulting solution is clear and colorless.

Add the Prosolv® SMCC 50 to a high shear granulator and slowly add the stabilizer solution using plow and chopper. After about 3 minutes a homogeneous mixture is obtained that is transferred to a small explosion proof fluid bed dryer. Dry the mixture at 60° C. regulating the airflow so that the powder becomes fluidized and swirls up and down in the expansion chamber. After about 10 minutes the mixture is completely dry and does not smell like ethanol anymore. The powder is screened through a 40 mesh screen and stored in a container for further processing.

Liothyronine sodium 0.015 mg and levothyroxine sodium 0.06 mg tablets (batch size 10,000 tbs.)

| | Per capsule | Per batch |
|---|---|---|
| Levothyroxine sodium titration (1%) from example 1. | 6.00 mg | 60.00 g |
| Liothyronine sodium titration (1%) | 1.50 mg | 15.00 g |
| SMCC/stabilizer mixture | 82.50 mg | 825.00 g |
| Ascorbic acid fine powder coated with Ethylcellulose, coating level ±5% w/w (antioxidant) | 5.00 mg | 50.00 g |
| Satialgine ™ H8 (alginic acid) | 4.00 mg | 40.00 g |
| Lubritab ® (hydrogenated vegetable oil) | 1.00 mg | 10.00 g |
| Total: | 100.00 mg | 1000.0 g |

The liothyronine sodium titration is made according to the procedure described in example 1.

Add to a small planetary blender Levothyroxine sodium titration (1%), Liothyronine sodium titration (1%), Ascorbic acid fine powder coated, Satialgine™ H8 and Lubritab®.

Blend this mixture for 10 minutes and compress into tablets with an average target weight of 100 mg using 9/32" diameter compression tooling.

The tablets so obtained contain ascorbic acid as an antioxidant. Ascorbic acid is an effective antioxidant but it is also a relatively strong acid. As such it is incompatible with the active ingredients with which it will interact through particle-to-particle contact.

This problem is circumvented by coating the ascorbic acid with ethylcellulose which isolates the ascorbic acid effectively, the coating is gas permeable and the antioxidant action is therefore preserved.

In this particular application both degradation pathways are inhibited, namely oxidation as well as deiodination.

This is accomplished using regular pharmaceutical production equipment using processes that can be scaled-up to large production size equipment.

The antioxidant can be added as an ingredient to the tablet but can also be added in a small container that is added to the finished product bottle. Ascorbic acid is the preferred antioxidant because it lacks toxicity, is effective and inexpensive. The ascorbic acid may be further activated by adding trace materials such as copper ions that renders the antioxidant even more effective.

The finished product container or bottle is an integral part of the finished product. Although it is demonstrated under example 1 that a standard polyethylene container may be sufficient to help provide product integrity, careful selected container materials will further aid in extending shelf life and protection for the product.

Such products that are impermeable to gases are aluminum, coated with vinyl or other suitable material, glass or plastic containers with increased wall thickness.

A finished product containing stabilizer and if desired, in combination with an antioxidant in a container that provides a superior barrier will address problems currently encountered by manufacturers and will also enable practitioners to better threat hypothyroidism and related illnesses. The prod-

EXAMPLE 4

Procedure for making a stabilized raw material concentrate containing 5% active ingredient.

| | |
|---|---:|
| Levothyroxine Sodium microfine (adjusted for water content) | 56.50 g |
| SMCC/stabilizer from example 3. | 100.00 g |
| SMCC/stabilizer from example 3. | 843.50 g |

Mix the Levothyroxine Sodium intensively with 100.00 g SMCC/stabilizer. Screen this mixture through a 60 mesh screen and add to a small v-Blender with intensifier bar. Add to the blender 843.50 g of SMCC/stabilizer and mix for 15 minutes with intensifier bar engaged.

Pass this mixture through a compactor using smooth rolls minimizing hydraulic force to assure that a compact but not extremely hard sheet is obtained. Mill the resulting sheet using a comill fitted with 0.075 grater screen and screen out the desired fraction, for example smaller that 60 mesh larger than 100 mesh and recycle material outside the range of this fraction until all material has been processed.

The granules can be used without further processing or coated if desired when excipients need to be used that are not compatible with the active.

The material obtained will allow for the preparation of a stable finished product with a minimum amount of iodide in the tablet or capsules eliminating the potential of unacceptable iodide intake as the result of medication, normal dietary intake and supplemental multivitamin/mineral preparations.

EXAMPLE 5

Procedure for making stabilized raw material concentrate containing 5% active ingredient.

| | |
|---|---:|
| Levothyroxine Sodium Microfine (adjusted for water content) | 56.50 g |
| Prosolv ™ SMCC 50 (Silicified Microcrystalline cellulose)0 | 912.00 g |
| Ethyl Cellulose | 30.00 g |
| Sodium Iodide | 1.50 g |
| Ethanol (99%) | 200.00 mL |
| Total: | 1000.00 G |

Dissolve the ethyl cellulose in alcohol and add the sodium iodide. Add the Prosolv™ and the levothyroxine to a high shear granulator. With plow and chopper engaged add the alcoholic solution of stabilizer and ethyl cellulose.

After about 3 minutes stop the granulator and pass the resulting granular mass through a 40 mesh screen. Transfer this mixer to a vacuum dryer and dry at room temperature for 1 hour under high vacuum. Dry until the residual alcohol content is less then 500 ppm.

The dry granulation can be further size for particular applications if necessary or processed into tablets or capsules after mixing with appropriate excipients.

This fine granular material can be easily mixed to form blends ready for direct compression. If desired the particles can be further processed by coating if an additional barrier is considered necessary. Other iodide salts may be used provided they are compatible with the actives and the excipients used. An example would be calcium iodide. The use of such alternative iodine salts would require studies to assure it is compatible with the medications at the given concentrations.

And as in the previous example, the iodine content is reduced to a level that is only a fraction of the RDA in the highest dosage form currently available of 300 mcg of medication. This invention effectively addresses current manufacturers problems of making a stable oral dosage form, potential FDA and Practitioners concerns regarding the intake of iodine in the form of acceptable iodide compounds.

I claim:

1. A method of making stabilized thyronine medications by combining together
   (a) Liothyronine Sodium
   (b) at least one iodine salt mixed with a carrier
   (c) a disintegrant
   (d) a lubricant
   (e) a binder, and
   (f) a filler.

2. A method of making stabilized thyroxine medications as defined in claim 1 with the additional step of
   combining levothyroxine sodium with said liothyronine sodium.

3. A method of making a stabilized thyroxine medication by combining together
   (a) Dextrothyroxine Sodium
   (b) at least one iodine salt
   (c) a disintegrant
   (d) a lubricant
   (e) a binder, and
   (f) a filler.

4. A stabilized thyroxine medication consisting of the combination of
   Levothyroxine Sodium,
   Liothyronine Sodium and
   at least one iodine salt.

5. A method of making stabilized thyroxine medications by combining together
   (a) thyroid
   (b) at least one iodine salt
   (c) a disintegrant
   (d) a lubricant
   (e) a binder and
   (f) a filler.

6. A method of making stabilized form of lithyronine sodium raw material by combining together:
   (d) Liothyronine sodium
   (e) A carrier material
   (f) Sodium iodide or other sutable iodide compound.

7. A method of making stabilized thyroid medications as defined in claims 1 or 3 by combining a antioxidant.

8. A method of making stabilized thyroid medications as defined in claims 1, 2, 3, or 4, wherein the medications are packaged in a high barrier container, and an antioxidant is added to the medications after they have been formed, which antioxidant is held serratly from the medications in a small container.

* * * * *